United States Patent [19]

Schmidt et al.

[11] Patent Number: 4,804,803
[45] Date of Patent: Feb. 14, 1989

[54] ISOMERIZATION WITH ONCE-THROUGH HYDROGEN

[75] Inventors: Robert J. Schmidt, Rolling Meadows; Lynn H. Rice, Palatine; Laurence Stine, Western Springs, all of Ill.

[73] Assignee: UOP Inc., Des Plaines, Ill.

[21] Appl. No.: 129,267

[22] Filed: Dec. 7, 1987

[51] Int. Cl.$^4$ .............................................. C10G 35/04
[52] U.S. Cl. ................................................... 585/748
[58] Field of Search ................. 208/139, 141; 585/748

[56] References Cited

U.S. PATENT DOCUMENTS

| | | | |
|---|---|---|---|
| 2,798,105 | 7/1957 | Heinemann et al. | 260/683.5 |
| 2,906,798 | 9/1959 | Starnes et al. | 260/683.65 |
| 2,993,938 | 7/1961 | Bloch et al. | 260/666 |
| 3,391,220 | 7/1968 | Haensel | 260/583.76 |
| 3,791,960 | 2/1974 | Davies et al. | 208/57 |
| 3,969,425 | 7/1976 | Hayes | 585/748 |
| 3,974,061 | 8/1976 | Quisenberry | 585/748 |
| 4,241,231 | 12/1980 | Gibson et al. | 585/748 |

Primary Examiner—Patrick P. Garvin
Assistant Examiner—George R. Fourson
Attorney, Agent, or Firm—Thomas K. McBride; John G. Tolomei

[57] ABSTRACT

A process for the isomerization of $C_4$-$C_6$ paraffins that uses a highly active catalyst to isomerize the feed in the presence of very little hydrogen. The process is characterized by good stability and high conversion with effluent hydrogen to hydrocarbon ratios of 0.05 or less. Continued operation at low hydrogen concentrations is made possible by the remarkably low coking tendency of the catalyst, especially during periods of temporary sulfur deactivation. The low hydrogen to hydrocarbon ratio simplifies the process and makes it cheaper to operate by eliminating facilities for the recovery and recycle of hydrogen.

5 Claims, 2 Drawing Sheets

ISOMERIZATION WITH ONCE-THROUGH HYDROGEN

BACKGROUND OF THE INVENTION

This invention relates generally to the isomerization of hydrocarbons. This invention relates more specifically to the isomerization of light paraffins using a solid catalyst.

DESCRIPTION OF THE PRIOR ART

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool normally includes $C_4$ and heavier hydrocarbons having boiling points of less than 205° C. (395° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the $C_6$ and heavier hydrocarbons can be upgraded into aromatics through hydrocyclization, the conversion $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons and reforming to convert $C_7$ and higher boiling hydrocarbons.

The isomerization of paraffins is a reversible first order reaction. The reaction is limited by thermodynamic equilibrium. The basic types of catalyst systems that are used in effecting the reaction is a hydrochloric acid promoted aluminum chloride system and a supported aluminum chloride catalyst. Either catalyst is very reactive and can generate undesirable side reactions such as disproportionation and cracking. These side reactions not only decrease the product yield but can form olefinic fragments that combine with the catalyst and shorten its life. One commonly practiced method of controlling these undesired reactions has been to carry out the reaction in the presence of hydrogen.

Isomerization processes that carry out the reaction in the presence of a halogenated platinum aluminum catalyst usually use a relatively high hydrogen to hydrocarbon ratio. U.S. Pat. No. 2,798,105 teaches the use of a platinum alumina catalyst in the isomerization of $C_4$–$C_5$ hydrocarbons with minor additions of molecular hydrogen to the reaction mixture and a hydrogen to hydrocarbon mole ratio of from 0.5 to 4. An isomerization of $C_4$–$C_7$ hydrocarbons using a low platinum content alumina catalyst with a halogen component and a minimum 0.17 hydrogen to hydrocarbon mole ratio is shown in U.S. Pat. No. 2,906,798. The addition of a halogen to an isomerization process is demonstrated in U.S. Pat. No. 2,993,938 where a catalyst having an aluminum base and platinum metal and a halogen incorporated thereon is used as an isomerization catalyst in a reaction that uses a 0.2 to 10 hydrogen to hydrocarbon mole ratio. Other isomerization references that teach the use of halogenated platinum alumina catalyst to isomerize $C_4$–$C_6$ hydrocarbons are U.S. Pat. Nos. 3,391,220 and 3,791,960 which teach a required hydrogen to hydrocarbon mole ratio ranging from 0.1 to 15. Thus, the art of isomerization has long recognized the usefulness of catalyst comprising a platinum group metal and a halogen on an alumina support for the isomerization of $C_4$–$C_6$ hydrocarbons. However, it has also been generally accepted that these processes require a relatively high ratio of hydrogen to hydrocarbon in order to obtain satisfactory catalyst life and product yields.

One reason for the use of a high hydrogen to hydrocarbon ratio stems from the high susceptibility of the typical platinum-alumina catalysts to sulfur deactivation. The presence of sulfur concentrations as low as 1 ppm can poison the platinum and lead to at least temporary deactivation of the catalyst. Rapid coking of the catalyst has been experienced in most cases following sulfur deactivation. If left unchecked, the coking will be severe enough to require a complete regeneration of the catalyst. The presence of a large excess of hydrogen will moderate or prevent catalyst deactivation during periods of temporary sulfur deactivation. Commercial processes have facilities for the treatment and removal of sulfur. Nevertheless, even with such facilities, it is inevitable that sulfur contamination will at times cause temporary catalyst deactivation. Therefore, it is common practice to maintain relatively high hydrogen/hydrocarbon ratios in the isomerization zone to ameliorate coking and avoid a full regeneration of the catalyst every time it is temporarily deactivated by sulfur.

Despite the need to maintain high hydrogen to hydrocarbon ratios and their susceptibility to sulfur deactivation, these halogenated platinum-alumina catalysts are generally favored for their high conversion and product yields. However, maintaining a relatively high hydrogen to hydrocarbon ratio adds to the cost and complexity of isomerization processes. Most of these costs are related to the recovery and recycling of the hydrogen to isomerization zone. Very little of the hydrogen that enters the isomerization zone is consumed in the process. Therefore, separation facilities are required to remove the hydrogen from the product effluent leaving the isomerization reaction zone. The recovered hydrogen can be recycled to the isomerization zone to minimize the addition of hydrogen to the process. However, compressor facilities must raise the pressure of the hydrogen gas before it is returned to the isomerization zone.

It is an object of this invention to provide a process for the isomerization of $C_4$–$C_6$ hydrocarbons that uses halogen and platinum group components on an alumina support and has good stability.

Another object of this invention is the elimination of recycle facilities for maintaining a high hydrogen to hydrocarbon ratio in an isomerization process.

BRIEF DESCRIPTION OF THE INVENTION

This invention is a process for isomerizing normal paraffins having 4–6 carbon atoms that achieves high conversion and good stability with a very low concentration of hydrogen. The invention uses a highly active chlorided platinum/aluminum catalyst in the isomerization reaction which has been discovered to retain its stability in the presence of hydrogen at or only slightly greater than the stoichiometric requirements for the isomerization reaction. Due to the susceptibility of this catalyst to sulfur deactivation and water poisoning, it is still necessary to treat the feed stream for water and sulfur removal. These treatments add to the expense of using such catalysts and decrease the economic benefits obtained thereby. The surprising ability of these catalysts to isomerize $C_4-C_7$ hydrocarbons over long periods of time without a large excess of hydrogen makes the use of such catalysts more attractive and offsets the detriments associated with water and sulfur removal. More surprisingly it has been discovered that this catalyst composition will experience very little coking when temporarily deactivated by sulfur. As a result, this process can operate with very low hydrogen/hydrocarbon ratios without risking the need for frequent regenerations.

Accordingly, in one embodiment, this invention is a process for isomerizing a feed stream containing $C_4-C_6$ normal hydrocarbons. The feed stream has a normal sulfur concentration of less than 0.5 ppm and a water concentration of less than 0.1 ppm. The feed stream is admixed with hydrogen to obtain a hydrogen to hydrocarbon ($H_2/HC$) ratio that will produce an effluent having a ($H_2/HC$) ratio of less than 0.05. The feed stream and hydrocarbon mixture are contacted in a reaction zone with an isomerization catalyst that comprises alumina having from 0.01 to 0.25 wt. of platinum and from 2 to 10 wt. % of a chloride component at isomerization conditions including a temperature in a range of from 40°–235° C. (104°–455° F.), a pressure of from 7 barsg to 70 barsg and a space velocity of from 0.1 to 10. A chloride concentration of from 30 to 300 ppm is maintained in the reaction zone. This effluent enters a stabilizer where it is separated into a product stream of $C_4-C_6$ hydrocarbons and a fuel gas stream which is removed from the process.

Other aspects of this invention relate to feed stream compositions, effluent stream compositions, reactor configurations, hydrogen concentrations, and catalyst details.

DETAILED DESCRIPTION OF THE INVENTION

Figure 1:
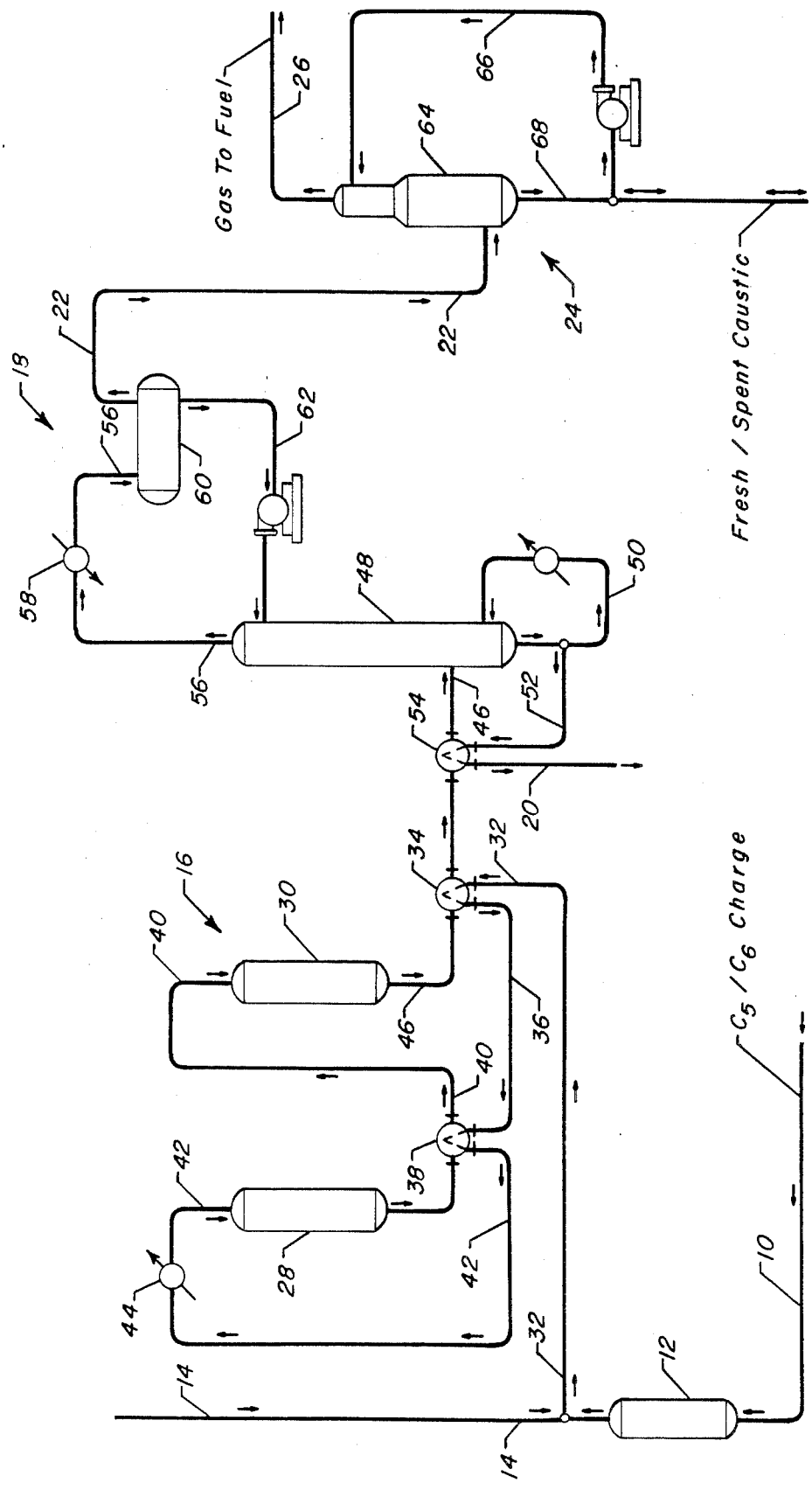
FIG. 1 schematically shows a process for isomerizing $C_5-C_6$ hydrocarbons. The feed stream enters a process through line 10 and passes through a dryer 12 for the removal of water and receives a small quantity of make-up hydrogen from a line 14. Feed and make-up hydrogen pass through a multi-stage reaction zone 16 and enter a stabilizer section 18. Line 20 takes a product stream comprising $C_5$ and $C_6$ hydrocarbons having an increased concentration relative to the feed stream of isoparaffins. Line 22 transfers net overhead from the stabilizer section to a scrubber section 24 that removes chloride compounds from the product stream and delivers a fuel gas through line 26.

The feedstocks that can be used in this invention include hydrocarbon fractions rich in $C_4-C_6$ normal paraffins. The term "rich" is defined to mean a stream having more than 50% of the mentioned component. Preferred feedstocks are substantially pure normal paraffin streams having from 4 to 6 carbon atoms or a mixture of such substantially pure normal paraffins. Other useful feedstocks include light natural gasoline, light straight run naphtha, gas oil condensate, light raffinates, light reformate, light hydrocarbons, field butanes, and straight run distillates having distillation end points of about 77° C. (170° F.) and containing substantial quantities of $C_4-C_6$ paraffins. The feed stream may also contain low concentrations of unsaturated hydrocarbons and hydrocarbons having more than 6 carbon atoms. The concentration of these materials should be limited to 10 wt. % for unsaturated compounds and 20 wt. % for heavier hydrocarbons in order to restrict hydrogen consumption and cracking reactions.

Hydrogen is admixed with the feed in an amount that will provide a hydrogen to hydrocarbon ratio equal to or less than 0.05 in the effluent from the isomerization zone. The hydrogen to hydrocarbon ratio of 0.05 or less at the effluent has been found to provide sufficient excess hydrogen for operation of the process. Although no net hydrogen is consumed in the isomerization reaction, the isomerization zone will have a net consumption of hydrogen often referred to as the stoichiometric hydrogen requirement which is associated with a number of side reactions that occur. These side reactions include cracking and disproportionation. Other reactors that will also consume hydrogen include olefin and aromatics saturation. For feeds having a low level of unsaturates, satisfying the stoichiometric hydrogen requirements demand a hydrogen to hydrocarbon ratio for the inlet stream of between 0.03 to 0.1. Hydrogen in excess of the stoichiometric amounts for the side reactions is maintained in the reaction zone to provide good stability and conversion by compensating for variations in feed stream compositions that alter the stoichiometric hydrogen requirements and to prolong catalyst life by suppressing these side reactions. If left unchecked, the side reactions reduce conversion and lead to the formation of carbonaceous compounds, usually referred to as coke, that foul the catalyst. It has now been found that the amount of hydrogen needed for suppressing coke formation need not exceed dissolved hydrogen levels. The amount of hydrogen in solution at the normal conditions of the isomerization zone effluent will usually be in a ratio of from about 0.02 to less than 0.01. The amount of excess hydrogen over the stoichiometric requirements that is required for good stability and conversion is in a ratio of hydrogen to hydrocarbons of from 0.01 to less than 0.05 as measured at the effluent of the isomerization zone. Adding the dissolved and excess hydrogen proportions show that the 0.05 hydrogen to hydrocarbon ratio at the effluent will satisfy these requirements for most feeds.

When the hydrogen to hydrocarbon ratio exceeds 0.05, it is not economically desirable to operate the isomerization process without the recycle of hydrogen to the isomerization zone. As the quantity of hydrogen leaving the product recovery section increases, additional amounts of $C_4$ and other product hydrocarbons are taken by the fuel gas stream from the product recovery section. The value of the lost product or the additional expense associated with recovery facilities to prevent the loss of product do not justify operating the process without recycle at hydrogen to hydrocarbon ratios above 0.05.

Hydrogen may be added to the feed mixture in any manner that provides the necessary control for the addition of small hydrogen quantities. Metering and monitoring devices for this purpose are well known by those skilled in the art. As currently practiced, a control valve is used to meter the addition of hydrogen to the feed mixture. The hydrogen concentration in the outlet stream or one of the outlet stream fractions is monitored by a hydrogen monitor and the control valve setting position is adjusted to maintain the desired hydrogen concentration. The direct effluent from the reaction zone contains a relatively high concentration of chlorides that can attack metal components of the monitor. Thus, the monitor preferably measures the concentration of hydrogen in a stream that has undergone caustic treatment for chloride removal such as a stabilizer off gas stream. The hydrogen concentration at the effluent is calculated on the basis of total effluent flow rates.

The hydrogen and hydrocarbon feed mixture is contacted in the reaction zone with an isomerization catalyst. The isomerization catalyst consists of a high chloride catalyst on an aluminum base containing platinum. The aluminum is an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process.

The catalyst also contains a chloride component. The chloride component termed in the art "a combined chloride" is present in an amount from about 2 to about 10 wt. % based upon the dry support material. The use of chloride in amounts greater than 5 wt. % have been found to be the most beneficial for this process.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the halogen. Halogen may also be added to the carrier material by contacting the calcined carrier material with an aqueous solution of the halogen acid such as hydrogen chloride, hydrogen fluoride, or hydrogen bromide.

It is generally known that high chlorided platinum-alumina catalysts of this type are highly sensitive to sulfur and oxygen-containing compounds. Therefore, the feedstock must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

Operating conditions within the isomerization zone are selected to maximize the production of isoalkane product from the feed components. Temperatures within the reaction zone will usually range from about 40°–235° C. (100°–455° F.). Lower reaction temperatures are generally preferred since they usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes temperatures in the range of from 60° to 160° C. are preferred. When it is desired to isomerize significant amounts of $C_4$ hydrocarbons, higher reaction temperatures are required to maintain catalyst activity. Thus, when the feed mixture contains significant portions of $C_4$–$C_6$ alkanes most suitable operating temperatures are in the range from 145° to 225° C. The reaction zone may be maintained over a wide range of pressures. Pressure conditions in the isomerization of $C_4$–$C_6$ paraffins range from 7 barsg to 70 barsg. Preferred pressures for this process are in the range of from 20 barsg to 30 barsg. The feed rate to the reaction zone can also vary over a wide range. These conditions include liquid hourly space velocities ranging from 0.5 to 12 hr.$^{-1}$, however, space velocities between 1 and 6 hr.$^{-1}$ are preferred.

Operation of the reaction zone also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

FIG. 1 shows a two-reactor system with a first stage reactor 28 and a second stage reactor 30 in the reaction zone. The catalyst used in the process is distributed equally between the two reactors. It is not necessary that the reaction be carried out in two reactors but the use of two reactors confer several benefits on the process. The use of two reactors and specialized valving (not shown) allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in the first vessel 28 with the rest of the reaction carried out in a final reactor stage at more favorable temperature conditions. FIG. 1 demonstrates this type of operation where the relatively cold hydrogen and hydrocarbon feed mixtures taken by line 32 are passed through a cold feed exchanger 34 that heats the incoming feed against the effluent from the final reactor 30. Line 36 carries the feed from the cold feed exchanger to the hot feed exchanger 38 where the feed is heated against the effluent carried from the first reactor 28 by line 40. Line 42 carries the partially heated feed from hot feed exchanger 42 through an inlet exchanger 44 that supplies any additional heat requirements for the feed and then into a first reactor 28. Effluent from first reactor 28 is carried to the second reactor 30 by line 40 after passage through exchanger 38 as previously described. Line 46 carries the isomerization zone effluent from second reactor 30 through cold feed exchanger 34 as previously described and into separation facilities.

At minimum, the separation facilities divide the reaction zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal isoalkanes. Normal isoalkanes recovered from the separation facilities may be recycled to the isomerization reaction zone to increase the conversion of normal alkanes to isoalkanes. The Figure shows separation facilities comprising a stabilizer section 18. Line 46 carries the effluent from second reactor 30 to a stabilizer column 48. Stabilizer column 48 is operated to deliver a bottoms fraction containing $C_4$ and heavier hydrocarbons and an overhead fraction $C_3$ hydrocarbons and lighter boiling compounds. The stabilizer column includes a reboiler loop 50 from which the $C_4+$ product stream is withdrawn by line 52. Products taken by line 52 pass through a product exchanger 54 that heats the reactor effluent before it enters column 48. Cooled product is recovered from exchanger 54 via product line 20. $C_3$ and lighter hydrocarbons and any excess hydrocarbons from the reaction zone are taken overhead from stabilizer column 48 through line 56, cooled in condenser 58 and separated into a gas stream and reflux by separator vessel 60. Line 62 returns reflux from vessel 60 to the top of column 48 and line 22 carries the net gas from separator drum 60 to scrubber section 24.

Scrubber section 24 contacts gas from drum 60 with a suitable treatment solution for neutralizing and/or removing acidic components that may have originated with the chloride addition to the isomerization zone and may be present in the gas stream. Typically, the treatment solution will be a caustic that is pumped around a contacting vessel 64 in a loop 66. Spent caustic is withdrawn and fresh caustic is added to the scrubber section by a line 68. After treatment in the scrubber section 24, the net gas is removed from the process via line 26. Gas recovered by line 26 will usually be put to use as a fuel.

EXAMPLE

Figure 2:
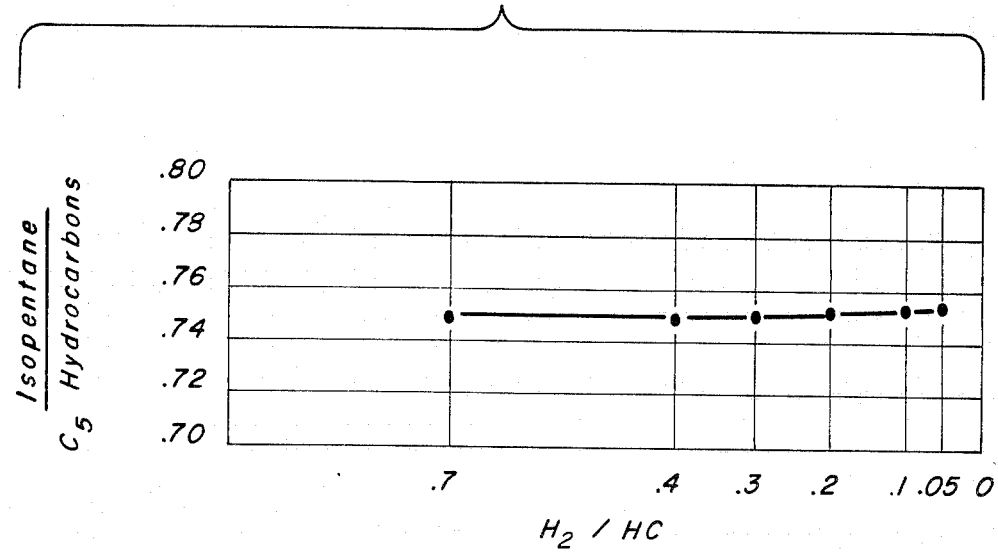
FIG. 2 contains a series of graphs showing input and output properties of the feed and effluent associated with a reaction zone of this invention and the prior art.
Figure 2:
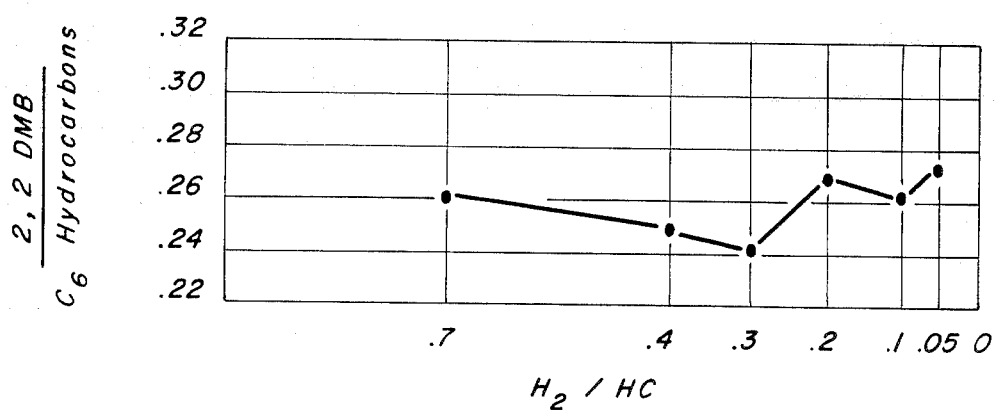
Figure 2:
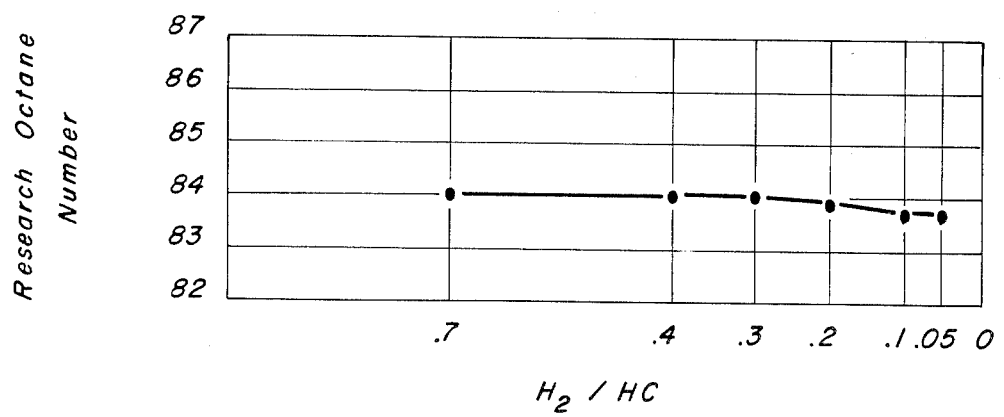

The process of this invention is characterized by high conversion, high selectivity, and good stability as can be seen from the following example. In this example, a hydrocarbon feed having an average composition given in the Table was charged to a two reactor zone system of the type shown generally in FIG. 1. Before entering the reaction zone, hydrogen was admixed with the hydrocarbon feed to provide indicated hydrogen to hydrocarbon ratios as given in FIG. 2 and ranging from 0.7 to 0.1 at the outlet of the reaction zone. Each reaction zone contained an alumina catalyst having 0.25 wt. % platinum and 5.5 wt. % chlorine.

TABLE

| Composition in wt. % | Reactor Charge |
| --- | --- |
| sp. gr. | 0.65 |
| $iC_4$ | 0.3 |
| $nC_4$ | 4.5 |
| $iC_5$ | 25.7 |
| $nC_5$ | 25.5 |
| CP | 1.4 |
| 22DMB | 0.9 |
| 23DMB | 1.5 |
| 2MP | 9.6 |
| 3MP | 6.5 |
| $nC_6$ | 15.7 |
| MCP | 6.0 |
| BZ | 1.4 |
| CH | 0.5 |
| $C7+$ | 0.1 |

The catalyst was prepared by vacuum impregnating an alumina base in a solution of chloroplatinic acid, 2% hydrochloric acid, and 3.5% nitric acid in a volume ratio of 9 parts solution to 10 parts base to obtain a peptized base material having a platinum to base ratio of approximately 0.9. The resulting mixture was cold-rolled for approximately 1 hour and evaporated until dry. Afterward, the catalyst was oxidized and the chloride content adjusted by contact with a 1M hydrochloric acid solution at 525° C. at a rate of 45 cc/hour for 2 hours. The catalyst was then reduced in electrolytic hydrogen at 565° C. for 1 hour and was found to contain approximately 0.25 wt. % Pt and approximately 1 wt. % chloride. Impregnation of active chloride to a level of approximately 5.5 wt. % was accomplished by sublimating aluminum chloride with hydrogen and contacting the catalyst with the sublimated aluminum chloride for approximately 45 minutes at 550° C.

The hydrocarbon feed mixture entered the first reaction zone at a temperature of approximately 160° C. The feed mixture at a temperature of approximately 175° C. was taken from the first reaction zone and after heat exchange with the incoming feed entered the second reaction zone at a temperature of approximately 140° C. The exit temperature of the second reaction zone was maintained at approximatey 140° C. and the feed passed through the reaction zones at a liquid hourly space velocity of about 2.4 hr.$^{-1}$. An average pressure of about 31 barsg was maintained in both reaction zones. The effluent from the second reaction zone was recovered at a temperature of about 140° C. At the beginning of the run, the $H_2/HC$ ratio at the outlet was kept at about 0.7 which corresponds to the typical range for a low $H_2/HC$ ratio as practiced in the prior art. Over a period of several months, the $H_2/HC$ ratio was lowered to the ratio of this invention. Average values for the isopentane to $C_5$ hydrocarbon ratio, 2,2-dimethylbutane to $C_6$ hydrocarbon ratio and research octane in the effluent were plotted at selected $H_2/HC$ ratios over the course of this run. As the data shows, the process of this invention was able to maintain substantially consistent values for these parameters as the $H_2/HC$ ratio was decreased. At the time of writing this application, the reactor system had experienced over 1200 hours of operation at a $H_2/HC$ ratio of about 0.05 without any appreciable loss of normal paraffin conversion or octane number reduction in the recovered effluent. Therefore, it has been shown that the process of this invention, using the catalyst as herein described, will provide a stable conversion of normal paraffins to isoparaffins at hydrogen addition levels that leave a ratio no more than 0.05 $H_2$ to hydrocarbon in the effluent.

What is claimed is:

1. A process for the isomerization of a feed stream comprising $C_4$–$C_6$ hydrocarbons and having a water concentration of less than 0.1 ppm, said process comprising:
    (a) adding hydrogen to said feed stream;
    (b) contacting said feed stream and hydrogen mixture in a reaction zone with an isomerization catalyst comprising alumina, having from 0.01 to 25 wt. % platinum and from 2 to 10 wt. % of a chloride component at isomerization conditions including a temperature in a range of from 40°–235° C. (104°–455° F.), a pressure of from 7 bars gauge to 70 bars gauge and a space velocity of from 0.1 to $10^{-1}$;
    (c) maintaining a chloride concentration in the reaction zone of from 30 to 300 ppm;
    (d) recovering an effluent stream from said reaction zone;
    (e) adjusting the amount of hydrogen added in step (a) so that said effluent stream has a hydrogen to hydrocarbon mol ratio of less than 0.05; and
    (f) separating said effluent stream in a stabilizer column into a product stream of $C_4$–$C_6$ hydrocarbons and a gas stream which is removed from the process without recycle of hydrogen.

2. The process of claim 1 wherein the hydrogen to hydrocarbon mol ratio of said feed stream is less than 0.1.

3. The process of claim 1 wherein said reaction zone includes a series of two reactors, the feed stream first enters a reactor operating at a temperature in the range of 120° to 225° C. and said effluent is recovered from a reactor operating at a temperature in the range of 60° to 160° C.

4. The process of claim 1 wherein said feed stream enters said reaction zone with a hydrogen concentration that exceeds the amount of hydrogen that is soluble in the feed stream by an amount equal to the stoichiometric hydrogen requirements of the feed stream.

5. The process of claim 1 wherein the alumina of said isomerization process comprises gamma-alumina.

* * * * *